United States Patent [19]
Kato et al.

[11] Patent Number: 5,814,568
[45] Date of Patent: Sep. 29, 1998

[54] WATER-ABSORBENT PAPER OF NONWOVEN FABIC FOR PREVENTING DISCOLORATION OF A LETTUCE STEM CUT SURFACE

[75] Inventors: Yoshitaka Kato, Yokohama; Atsushi Hishiki, Omiya, both of Japan

[73] Assignee: Asahi Kasei Kogyo Kabushiki Kaisha, Osaka, Japan

[21] Appl. No.: 750,562

[22] PCT Filed: Jun. 12, 1995

[86] PCT No.: PCT/JP95/01170

§ 371 Date: Dec. 16, 1996

§ 102(e) Date: Dec. 16, 1996

[87] PCT Pub. No.: WO96/00004

PCT Pub. Date: Jan. 4, 1996

[30] Foreign Application Priority Data

Jun. 27, 1994 [JP] Japan ................................ 6-144561

[51] Int. Cl.[6] .......................... D04H 1/58; C07D 315/00; A01N 3/00
[52] U.S. Cl. ............................ 442/123; 549/416; 428/17; 428/22

[58] Field of Search ............................ 442/123; 549/416; 428/17, 22

[56] References Cited

FOREIGN PATENT DOCUMENTS

| | | |
|---|---|---|
| 58-40035 | 3/1983 | Japan . |
| 58-51842 | 3/1983 | Japan . |
| 61-108359 | 5/1986 | Japan . |
| 61-268601 | 11/1986 | Japan . |
| 1 6034 | 1/1989 | Japan . |
| 1-258602 | 10/1989 | Japan . |
| 2 135045 | 5/1990 | Japan . |
| 2-138533 | 11/1990 | Japan . |
| 2 303469 | 12/1990 | Japan . |
| 2-291226 | 12/1990 | Japan . |
| 4-148643 | 5/1992 | Japan . |

*Primary Examiner*—Terrel Morris
*Attorney, Agent, or Firm*—Birch, Stewart, Kolasch & Birch, LLP

[57] ABSTRACT

A water-absorbent paper or nonwoven fabric containing 5-hydroxy-2-hydroxymethyl-γ-pyrone for preventing the discoloration of the cut surface of lettuce stem and further containing an organic acid having from 2 to 10 carbon atoms and/or a water-retaining agent.

15 Claims, No Drawings

WATER-ABSORBENT PAPER OF NONWOVEN FABIC FOR PREVENTING DISCOLORATION OF A LETTUCE STEM CUT SURFACE

TECHNICAL FIELD

The present invention relates to a water-absorbent paper or nonwoven fabric for preventing the discoloration of the cut surface of lettuce stem and a method for preventing the discoloration thereof.

BACKGROUND ART

Various methods have been proposed to retain the freshness of vegetables or fruits or to prevent them from becoming moldy. For example, JP-A-2-303469 discloses a method for packaging a processed "wasabi" (Japanese horseradish) or mustard along with a preservative. JP-A-58-51842 discloses a method for retaining the freshness of vegetables or fruits which comprises applying to the cut surface of their roots or stems, a very small amount of a powder, aqueous solution, glycol solution or alcohol solution obtained by mixing an oxide, peroxide, polysaccharide, gum, metal salt, formaldehyde, urotropin or the like with an organic acid such as malic acid, tartaric acid, citric acid or the like and tightly packaging them respectively in a polystyrene film or the like. JP-A-64-6034 discloses a method for retaining the freshness of vegetables, fruits or cut flowers by packaging them respectively in a plastic sheet (or film) to which 5-hydroxy-2-hydroxymethyl-γ-pyrone is applied.

However, the methods mentioned above are not satisfactory to prevent the cut surface of lettuce stem from discoloring. An object of the present invention is to improve the effects of preventing the discoloration of the cut surface of lettuce stem.

DISCLOSURE OF THE INVENTION

The present inventors have accomplished the present invention as a result of massive research to overcome the drawbacks of the prior art described hereinbefore.

The present invention provides a water-absorbent paper or nonwoven fabric containing 5-hydroxy-2-hydroxymethyl-γ-pyrone for preventing the discoloration of the cut surface of vegetables, fruits and cut flowers and a method for preventing discoloration by the use thereof.

5-Hydroxy-2-hydroxymethyl-γ-pyrone used in the present invention (hereinafter referred to as the pyrone compound) is represented by the following formula (1) and is also called kojic acid. This compound is produced from various carbohydrates by the use of a microorganism and is commercially available.

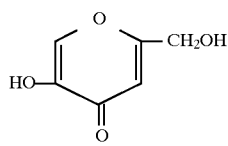

(1)

The water absorption ratio of the water-absorbent paper or nonwoven fabric of the present invention is not less than 60 percent, preferably not less than 80%, as determined by the measurement method described below.

In the present invention, it is necessary that the pyrone compound be impregnated in the water-absorbent paper or nonwoven fabric. The impregnation of the pyrone compound in the water-absorbent paper or nonwoven fabric of the present invention makes it possible to maintain or enhance freshness-retaining effects such as prevention of leaf wilting and rotting and to further prevent the cut surface from discoloring, as compared with the application of the pyrone compound to a plastic film or sheet having less than 60% of water absorption ratio or the direct application of the pyrone compound to lettuce stem. The reason why a discoloration-preventing effect is exhibited is not clear, but it is presumably attributed to the synergism of the antibacterial effects of 5-hydroxy-2-hydroxymethyl-γ-pyrone and the action by the water-absorbent paper or nonwoven fabric of absorbing and removing a browning enzyme.

The content of the pyrone compound in the water-absorbent sheet is preferably less than 8 g/m², more preferably 0.05–5 g/m².

The nonwoven fabric used in the present invention is composed of short or long fibers of cotton, rayon, acetate, nylon, polyester or the like, but its fiber density and production method are not limited, particularly if its water absorption ratio is within the scope of the present invention.

Referring to the method for impregnating the pyrone compound into the water-absorbent paper or nonwoven fabric, it is preferred to apply it as a solution or dispersion obtained by dissolving or dispersing the pyrone compound in water, an alcohol, an acetic acid ester or the like. Besides the ordinary application with a brush or the like, a method of either immersing the water-absorbent sheet in the solution or dispersion or passing it through the solution or dispersion may also be adopted.

In order to further enhance the freshness retaining effects, it is preferred to further impregnate the water-absorbent sheet with an additional organic acid and/or water-retaining agent in addition to 5-hydroxy-2-hydroxymethyl-γ-pyrone. For this purpose, it is advisable to add an additional organic acid and/or water-retaining agent to the solution or dispersion of the pyrone compound of the present invention.

Additional organic acids include those having from 2 to 10 carbon atoms and may be preferably selected from food additives, such as adipic acid, citric acid, tartaric acid, vitamin C, etc., from the viewpoint of food hygiene. The content of the additional organic acids is preferably from 0.03 to 8 g/m² of the water-absorbent sheet, more preferably from 0.1 to 5 g/m².

As water-retaining agents, hygroscopic salts such as calcium chloride, magnesium chloride, sodium chloride, etc. and dextrin may be used. Dextrin is particularly preferred as a water-retaining agent from the viewpoint of adhesion to the water-absorbent paper or nonwoven fabric. The content of the water-retaining agents in the water-absorbent sheet is preferably from 0.03 to 8 g/m², more preferably from 0.1 to 5 g/m².

The most effective method for preventing the discoloration of the cut surface of the lettuce stem with the water-absorbent paper or nonwoven fabric of the present invention is to have the water-absorbent paper or nonwoven fabric substantially in contact with the cut surface. By "substantially in contact" is meant either covering the cut surface with the water-absorbent sheet to an extent sufficient to prevent discoloration or contacting all or part of the cut surface with the water-absorbent sheet.

BEST MODE FOR CARRYING OUT THE INVENTION (Working Example)

Various embodiments of the present invention are specifically described with reference to the following examples.

The following is the method for determining the water absorption ratio.

A rectangular water-absorbent paper or nonwoven fabric specimen, 20 by 25 cm, is immersed in water of 20° C. for one minute and taken out of the water, and non-absorbed water is removed from both surfaces thereof. The water absorption ratio is obtained from the following formula.

Water absorption ratio $= (B-A) \times 100/A$

A: Weight (g) of absorbent sheet before water absorption

B: Weight (g) of absorbent sheet after water absorption (Examples 1–4 and Comparative Examples 1–3)

Compounds in amounts shown in Table 1 in the form of an aqueous solution were applied to paper, nonwoven rayon fabric or plastic film specimens. Each of the specimens was then applied to the cut surface of a lettuce stem so that the cut surface could be covered with the specimen. Each of the thus treated lettuce was wrapped in a polystyrene film and allowed to stand at a temperature of 25° C. and a relative humidity of 70%. The deterioration of the freshness of each cut surface over time was evaluated and the evaluation results are shown in Table 1. Each evaluation result indicates the average of ten values obtained by evaluating ten lettuce samples per specimen according to the following classification.

| Classification | Description |
| --- | --- |
| 5 | No deterioration; same as at time of wrapping |
| 4 | Almost no deterioration; nearly the same as at time of wrapping |
| 3 | Some deterioration, but quite marketable |
| 2 | Manifest deterioration, barely marketable |
| 1 | Remarkable deterioration, not marketable |

Utilization Field in Industry

As compared with the prior art, the present invention provides freshness-retaining effects such as the prevention of leaf wilting or rotting of lettuce and further provides the effects of preventing discoloration of the cut surface.

TABLE 1

|  |  | Compound applied | Amount applied (g/m$^2$) | Substrate | Absorption ratio (%) | Leaf wilting | |
| --- | --- | --- | --- | --- | --- | --- | --- |
|  |  |  |  |  |  | 1 day after wrapping | 4 days after wrapping |
| Example | 1 | Kojic acid[1] | 0.5 | Paper (45 g/m$^2$) | 130 | 4.2 | 3.3 |
|  | 2 | Same as above | 0.5 | Nonwoven rayon fabric (100 g/m$^2$) | 95 | 4.1 | 3.4 |
|  | 3 | Kojic acid Citric acid | 0.5 0.8 | Paper (45 g/m$^2$) | 130 | 4.2 | 3.4 |
|  | 4 | Kojic acid Tartaric acid Dextrin | 0.5 0.8 0.8 | Paper (45 g/m$^2$) | 130 | 4.3 | 3.4 |
| Comparative Example | 1 | None |  |  |  | 3.8 | 3.1 |
|  | 2 | Kojic acid | 0.3 | Polystyrene film 20μ | 0 | 4.0 | 3.3 |
|  | 3 | Hinokithiol | 0.5 | Paper (45 g/m$^2$) | 130 | 4.2 | 3.3 |

| |  | Evaluation Results | | | | | |
| --- | --- | --- | --- | --- | --- | --- | --- |
| | | Leaf yellowing | | Leaf rooting | | Cut surface discoloration | |
| | | 1 day after wrapping | 4 days after wrapping | 1 day after wrapping | 4 days after wrapping | 1 day after wrapping | 4 days after wrapping |
| Example | 1 | 4.3 | 3.7 | 4.3 | 3.7 | 4.7 | 4.0 |
|  | 2 | 4.3 | 3.7 | 4.3 | 3.7 | 4.7 | 4.0 |
|  | 3 | 4.4 | 3.8 | 4.5 | 3.7 | 4.9 | 4.1 |
|  | 4 | 4.5 | 3.9 | 4.5 | 3.8 | 5.0 | 4.2 |
| Comparative Example | 1 | 3.8 | 3.2 | 4.0 | 3.4 | 3.8 | 1.0 |
|  | 2 | 4.0 | 3.5 | 4.0 | 3.5 | 4.0 | 1.5 |
|  | 3 | 4.2 | 3.8 | 4.5 | 3.9 | 4.2 | 2.0 |

[1]Kojic acid: 5-Hydroxy-2-hydroxymethyl-γ-pyrone

We claim:

1. A water-absorbent paper or nonwoven fabric containing 5-hydroxy-2-hydroxymethyl-γ-pyrone for preventing the discoloration of the cut surface of lettuce stem and further containing an organic acid having from 2 to 10 carbon atoms and/or a water-retaining agent.

2. The water-absorbent paper or nonwoven fabric according to claim 1, wherein the content of 5-hydroxy-2-hydroxymethyl-γ-pyrone in the water-absorbent paper or nonwoven fabric is less than 8 g/m$^2$.

3. The water-absorbent paper or nonwoven fabric according to claim 1, wherein the content of 5-hydroxy-2-hydroxymethyl-γ-pyrone in the water-absorbent paper or nonwoven fabric is from 0.05 to 5 g/m$^2$.

4. The water-absorbent paper or nonwoven fabric according to claim 3, wherein the water absorptivity of the water-absorbent paper or nonwoven fabric is not less than 80 percent by weight, based on the respective weights of the water-absorbent paper or the nonwoven fabric, before an absorption of water therewith.

5. The water-absorbent paper or non-woven fabric according to claim 1, wherein the organic acid having from 2 to 10 carbon atoms is selected from the group consisting of adipic acid, citric acid, tartaric acid and vitamin C.

6. The water-absorbent paper or nonwoven fabric according to claim 1, wherein the water-retaining agent is selected from the group consisting of calcium chloride, magnesium chloride, sodium chloride and dextrin.

7. The water-absorbent paper or nonwoven fabric according to claim 6, wherein the water-retaining agent is dextrin.

8. A method for preventing the discoloration of the cut surface of lettuce stem which comprises bringing a water-absorbent paper or nonwoven fabric containing 5-hydroxy-2-hydroxymethyl-γ-pyrone into substantial contact with the cut surface of the lettuce stem.

9. The method for preventing the discoloration according to claim 8, wherein the content of 5-hydroxy-2-hydroxymethyl-γ-pyrone in the water-absorbent sheet is less than 8 g/m$^2$.

10. The method for preventing the discoloration according to claim 8, wherein the content of 5-hydroxy-2-hydroxymethyl-γ-pyrone in the water-absorbent sheet is from 0.05 to 5 g/m$^2$.

11. The method for preventing the discoloration according to claim 10, wherein the water absorptivity of the water-absorbent paper or nonwoven fabric is not less than 80 percent by weight, based on the respective weights of the water-absorbent paper or the nonwoven fabric, before an absorption of water therewith.

12. The method for preventing the discoloration according to claim 10, wherein the water-absorbent paper or nonwoven fabric further contains an additional organic acid having from 2 to 10 carbon atoms and/or a water-retaining agent.

13. The method for preventing the discoloration according to claim 12, wherein the organic acid having from 2 to 10 carbon atoms is selected from the group consisting of adipic acid, citric acid, tartaric acid and vitamin C.

14. The method for preventing the discoloration according to claim 12, wherein the water-retaining agent is selected from the group consisting of calcium chloride, magnesium chloride, sodium chloride and dextrin.

15. The method for preventing the discoloration according to claim 14, wherein the water-retaining agent is dextrin.

\* \* \* \* \*